United States Patent [19]

Al Ani

[11] 3,948,265

[45] Apr. 6, 1976

[54] MEDICATED APPLICATOR

[76] Inventor: Safwat Daoud Al Ani, Dr Lindhsgata 1, Goteborg, Sweden, 41325

[22] Filed: Aug. 27, 1974

[21] Appl. No.: 501,073

[30] Foreign Application Priority Data

Aug. 31, 1973 Sweden............................ 7311859

[52] U.S. Cl. ............................................. 128/267
[51] Int. Cl.² ......................................... A61M 7/00
[58] Field of Search ............. 128/267, 260; 401/128

[56] References Cited
UNITED STATES PATENTS

| | | | |
|---|---|---|---|
| 1,712,667 | 5/1929 | Hart................................... | 401/128 |
| 2,157,743 | 5/1939 | Temple............................. | 128/267 X |
| 3,327,706 | 6/1967 | Watson............................. | 128/267 |
| 3,506,009 | 4/1970 | Pietro............................... | 128/267 |

*Primary Examiner*—Aldrich F. Medbery
*Attorney, Agent, or Firm*—Holman & Stern

[57] ABSTRACT

Implements for application of styptics, cosmetics and therapeutically and/or diagnostically active substances have since long times been used with good results. Such implements are in the following referred to as applicators, which comprise a carrier in the form of a stick, a strip or the like, carrying at least at one end an amount of the substance in question.

Earlier applicators suffer from the drawbacks that they are difficult to keep sterile and that it is not possible to apply accurately measured doses by means thereof. In order to improve these properties it is now provided an applicator of the kind referred to the carrier of which at least at one surface portion being provided with a thin, homogeneous layer of an active substance in a dried and liquid-soluble state. The carrier itself or at least the portion thereof covered by the substance being incapable of absorbing any liquid and thus allowing all the substance applied thereto to be dissolved by the moisture of a moist body tissue or the like and thus be transferred thereto.

5 Claims, 2 Drawing Figures

MEDICATED APPLICATOR

BACKGROUND OF THE APPLICATION

Various kinds of applicators are used for styptic or cosmetic purposes such as the wooden stick on one end of which a cotton wad in the form of a little bud, is mounted. This cottonbud stick is used to absorb or remove unwanted fluids or materials such as water, pus, plasma or blood, or wax from the ear. It is also known to apply medicaments or cosmetics by dipping the stick bud in a solution and then apply it onto the area to be treated. These cotton-bud sticks can be packaged sterile in air-tight and moisture-tight packages. A disadvantage of these sticks is however that they can not be used for application of rather small doses of an active substance such as for instance a few milligrams only. Therefore only a rough dosage of for instance one or two drops of the solution can be delivered. This is natural as the substances applied on the cotton bud are either in the dry state and have to be immerced in a liquid such as water for being dissolved before application, or in the liquid state packaged in a moisture-tight package, and in either case the amount of the substance which can be obtained from the cotton wad depends on the amount of water present at that particular time. When the moist cotton stick is packaged and stored for a long time, the amount of water is expected to decrease and subsequently the amount of the substance which can be obtained is much less compared to freshly prepared one. Therefore the amount of the active substance that can be transferred from the cotton bud to the body tissue depends on the amount of the water present, and consequently, the amount of the substance delivered varies accordingly, whereby correct doses and especially smaller doses would be impossible to obtain.

A further disadvantage of sticks with cotton buds is that the cotton fibres are liable to get loose and by touching the body tissues may fall off into the tissue. This is very objectionable especially during operations such as operations on the eye.

Another disadvantage is that the active substance may react with either the wooden stick or the cotton fibres, whereby the chemical properties of the substance may change and unwanted by-products may probably be produced at such reactions.

As mentioned above, styptic sticks are already known, and used for styptic purposes. At one end of a disposable styptic stick or strip, a water soluble styptic substance such as alum is applied by repeated dipping in a solution of the substance until a small ball or pellet of the styptic material is formed. By using such styptic sticks, the ball is dipped in water and applied immediately onto the bleeding spot in order to stop the bleeding. The stick thereafter is discarded.

A similar disadvantage as of the cotton-bud sticks is that the dose delivered by the styptic stick is uncontrollable because the amount of styptic material dissolved is not always the same. The delivery of rather small or more accurate doses which is one aim of this invention can not be accomplished either by the cotton-bud sticks or by the styptic sticks.

At most applicators of the kind referred to a preservative must be added to the active substance to minimize the oxidative processes and to prolong the shelf-life of the applicator. The addition of preservatives to the medicaments is however a disadvantage because of the danger of sensitization of the body to the preservative substances, or the danger of their direct toxic effects on the tissues. This disadvantage is present not only at the above mentioned moist cotton-bud sticks but also at almost all medical solutions which are not selfsterilizing, such as eye-drops, nose-drops etc.

A very common method of drug administration is the topical direct application of the medicament in solution form on the skin and mucous membrances, into the eye, nose, throat or vagina etc. The hitherto most common method to apply such medicaments has been to drop a solution of the medicament directly onto the application spot. This is efficient, but the instillation of eye-drops usually provokes tearing reflexes due to the known smarting pain caused by the drops. This in turn causes an increased tear flow and consequently a dilution of the medicament applied. Due to the reflex pain the patient will furthermore screw up his eyes so that the eye-drops and the tears run outside the eye whereby the quantity of the applied substance remaining in the eye is much less and the doses hereby become quite uncontrollable and hence the effect of the medication is uncertain and of very short duration. Another disadvantage by using the conventional eye-drops is that there is always risk for contamination. At surgical operations on the eye it is for instance a requirement to use active substances without addition of preservatives, which means that it is necessary at such operations to use freshly prepared eye-drops because of their short shelf-life. It is very difficult to keep medicaments sterile in solution and at an investigation there has even been found bacteria in new unopened eye-drops bottles. Contamination of the eyedrops even by non-pathogenic bacteria may cause a change in the pH-value of the solution and as a result of this an unfavourable change of the medicament will occur. Bacterial endproducts would be formed, which also can be irritating for the body tissue, e.g. the eyes.

SUMMARY OF THE INVENTION

The purpose of the invention is to provide an applicator which eliminates the above mentioned drawbacks and by means of which a rather accurate dose of a therapeutically and/or diagnostically active substance, can be applied to the body tissue without causing too much pain or irritation. Another purpose of the invention is to provide an applicator which may carry as little of the active substance as to equal one dose, and still another purpose is to propose an applicator ensuring the use of active substances without addition of preservatives.

The active substance shall be easily applicable with very great precision also in areas which are difficult to reach and the substances shall have a good durability also without addition of preservatives. The applicator should furthermore be easy to keep sterile, in order to reduce the risk of contamination. This task is solved by the invention thereby that said active substance is applied to one or both ends, one end surface or one surface section of said carrier in a very thin, homogeneous, dry and liquid-soluble layer of such a quantity as to correspond substantially to one dose for one specific occasion of use, at least said one end, end surface or surface section of the carrier which is provided with the active substance being non-liquid-absorbing.

DESCRIPTION OF THE PREFERRED EMBODIMENTS

Figure 1:
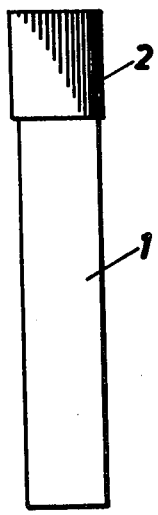
FIG. 1 shows in a schematic side elevation one embodiment of an applicator according to the invention.
Figure 2:
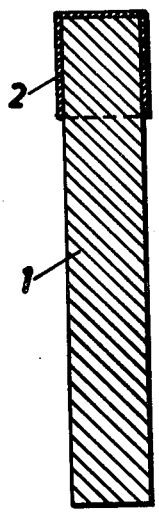
FIG. 2 is a sectional view of the applicator shown in FIG. 1.

The inventive applicator shown in the drawings annexed hereto is shaped as a longitudinal carrier 1, having at one end, a very thin, homogeneous layer 2 of a dried and liquid-soluble therapeutically and/or diagnostically active substance. The schematic applicator shown in the drawings is only an example which may not be considered as a restriction of the scope of invention.

The applicator according to the invention, i.e. the carrier of the active substance is made of a suitable material such as glass, plastics or the like, which material is not liquid-absorbing. If for economical reasons a cheaper material such as paper, wood, fibres (natural or synthetic) or the like is used, then the end portion(s) of said material intended to carry the active substance must be prepared in such a manner that said portion becomes not liquid-absorbing. The shape and size of the applicator varies due to the field of application.

Applicators which for instance shall be used in the eye can be made small, some centimeters long and one or two mm in diameter, in the form of a rod with pointed or blunt end(s), whereas applicators which shall be used for instance in vagina on the other hand ought to be made longer than the eye applicators and they shall also have a more robust form.

The applicator end or ends can for instance be pointed blunt, spheric or they can be given the form of a spatula or any other form suitable for the application purpose. The handle of the applicator — the carrier — can be straight or bent to any form in order to obtain the easiest or the best way of application for different purposes.

The active substance (the medicaments) are applied at the end(s) of the appplicator in small doses for the intended purpose. The active substances may if it is necessary be mixed with other substances e.g. preservatives, neutral substances such as viscosity improving material, binders, adhesives etc.

Application of the active substances is carried out by means of any suitable application method e.g. by controlled dipping of the ends of the applicator in a solution of the substances, by means of spraying a substance onto the applicator or by fitting to the applicator by means of a suitable adhesive a dried, active substance, in such a manner that the final applicator carries a measured amount of the substance(s) in question.

Sterilization of the applicators shall be carried out according to wellknown methods either before or preferably after the applicator has been packed. The method of sterilization is also dependent on the properties of the active substance and on the nature of the packing.

The packing of the applicators after application and drying of the active substances shall preferably be as air-tight as possible in order to prevent the substances from contact with moisture and gases in the environment. The substances shall also if so required be protected from light and any other harmful environmental factors.

The packing can be a one-dose-disposable packing whereby cross infection can be eliminated. The packing however may contain several applicators in one pack for instance for hospital use.

The packing can be composed of one or more containers due to the field of use. At surgical operations several containers are required in order to minimize or preclude the risk of contamination when the packing is opened. The packing can be made of any suitable material e.g. plastic or metal foil, paper or the like.

The technic of using the inventive applicator is very easy to learn. The applicator is pulled out from its package and the end of the applicator on which the active substances already are applied is brought into contact with the moist tissue area whereby the rapidly soluble substances are dissolved. If the substance shall be applied onto dry body tissues it is possible to supply the tissue area with a drop of a suitable dissolving liquid as for instance water or a sodium chloride solution.

The inventive applicator has the following advantages.

The active substances — the medicaments — maintain their properties much longer when in a dry and sterile state as compared to when in liquid form. The applicators are further protected from light, the humidity and bacteria in air-tight packages.

It is very easy for the layman and for the hospital personnel to learn how to use the applicator. The patient need not lay down during the application. He may instead treat himself with the applicators which is generally difficult when using eye drops especially if the patient is old.

The inventive applicators are not irritant for the eyes to the same extent as conventional eye-drops which oftenly contain preservatives which will cause the eyes further irritation and pain directly following the instillation of the eye-drops. The patient will screw up his eye immediately and the eye drops will flow out. The inventive applicators on the other hand contain only such active substances which generally give only a mild irritation. The tear flow will never be so large that the tears run out and the treatment is therefore more efficient. The applicators are ideal for the treatment of children.

As mentioned above it is hardly necessary to wipe off the eyes after treatment with these applicators due to minimal irritation. That means that almost the whole amount of the active substance applied will be kept inside the conjunctival sac and more exact dosage of the medicaments can be achieved as compared to using conventional eye drops.

When using rose Bengal and fluorescein eye drops the eye lids and the face become discoloured which is very displeasing for the patient. When applying the same dyes with the inventive applicators there will be practically no discolouring of the eyelids or the face.

Due to lesser tear flow when using the applicators there will be no tears running out of the eye and the medicaments will have less contact with the skin of the face which will reduce the danger of contact eczema at the eye lids and in the face.

Allergic contact eczema is common especially among patients using eye drops and ointments for longer periods, e.g. patients with glaucoma. This risk for contact eczema can be substantially reduced if not eliminated due to the new application technic. The active substance applied on the applicator is rubber against the conjunctiva of the lower eye lid and is entirely dissolved in the tears without causing an increase of the tear flow.

The inventive applicators are economical to use in hospitals and at doctor's offices. The eye-drops bottles are usually thrown away one month after opening the container in order to avoid the danger of contamination. The applicators are packed under sterile conditions in a single dose discardable packing, which will entirely eliminate the risk of contamination. The dry medicaments on the applicator are further protected from the harmful environmental factors which ensures a much longer shelf-life than for the eye-drops.

The inventive applicators are also economical for use at home, as the waste percentage is much lower and the life span is much longer. The amount of substance on the applicators needed for a certain period of treatment is much less than the corresponding amount in solution in an eye-drops bottle in which case the costs of the applicators would be less than that of the eye-drops.

As can be seen from the above description, the medicated applicators of this invention is convenient to carry, as in the pocket or purse, is readily available and sanitary and provides a fresh medicament for each use.

The inventive applicators are handy and can be used swiftly which means that time is saved which is especially appreciated by the busy ophtalmologist, the general practitioner and the hospital personnel.

What we claim is:

1. An applicator for application of active substances which have therapeutic and diagnostic properties onto body tissues comprising an elongated carrier provided on a portion of the surface of at least one end of said carrier with said active substance in a very thin, homogeneous, dry, liquid soluble layer of such a quantity as to correspond substantially to one precise dose for one specific occasion of use, said surface of said carrier which is provided with the active substance being non-liquid-absorbing.

2. The applicator as claimed in claim 1, wherein the carrier is manufactured from a non-liquid-absorbing material without pores and having a smooth surface.

3. The applicator as claimed in claim 1, wherein the said applicator is made of a liquid-absorbing material, and that the carrier is prepared so as to render it now-liquid-absorbing, at least in the region provided for applying the active substance.

4. The applicator as claimed in claim 2 wherein said non-liquid-absorbing material is glass.

5. The applicator as claimed in claim 2 wherein said non-liquid-absorbing material is plastic.

* * * * *